United States Patent
Wang et al.

(10) Patent No.: US 10,470,676 B2
(45) Date of Patent: Nov. 12, 2019

(54) NONINVASIVE 4-D TIME-RESOLVED DYNAMIC MAGNETIC RESONANCE ANGIOGRAPHY

(71) Applicants: THE REGENTS OF THE UNIVERSITY OF CALIFORNIA, Oakland, CA (US); THE TRUSTEES OF THE UNIVERSITY OF PENNSYLVANIA, Philadelphia, PA (US)

(72) Inventors: Danny J J Wang, Oak Park, CA (US); Lirong Yan, Los Angeles, CA (US); Hee Kwon Song, Moorestown, NJ (US)

(73) Assignees: THE REGENTS OF THE UNIVERSITY OF CALIFORNIA, Oakland, CA (US); THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 746 days.

(21) Appl. No.: 14/721,546

(22) Filed: May 26, 2015

(65) Prior Publication Data

US 2015/0327783 A1    Nov. 19, 2015

Related U.S. Application Data

(63) Continuation of application No. PCT/US2013/071590, filed on Nov. 25, 2013.
(Continued)

(51) Int. Cl.
    *G01R 33/48* (2006.01)
    *A61B 5/026* (2006.01)
(Continued)

(52) U.S. Cl.
    CPC ............ *A61B 5/0263* (2013.01); *A61B 5/055* (2013.01); *G01R 33/4806* (2013.01);
(Continued)

(58) Field of Classification Search
    CPC .................................................. G01R 33/4818
    See application file for complete search history.

(56) References Cited

U.S. PATENT DOCUMENTS 5,377,680 A * 1/1995 Bernstein ............. A61B 5/0555
                                                          600/413
7,277,597 B2 * 10/2007 Lee ..................... G01R 33/4824
                                                          382/280
(Continued)

FOREIGN PATENT DOCUMENTS

JP     2004-016613 A     1/2004
KR     10-2010-002148 A  1/2010

OTHER PUBLICATIONS

Song et al., Dynamic MRI with Projection Reconstruction and KWIC Processing for Simultaneous High Spatial and Temporal Resolution, Magnetic Resonance in medicine (2004) 52:815-824.*
(Continued)

*Primary Examiner* — Luther Behringer
(74) *Attorney, Agent, or Firm* — O'Banion & Ritchey LLP; John P. O'Banion

(57) ABSTRACT

A method for non-contrast enhanced 4D time resolved dynamic magnetic resonance angiography using arterial spin labeling of blood water as an endogenous tracer and a multiphase balanced steady state free precession readout is presented. Imaging can be accelerated with dynamic golden angle radial acquisitions and k-space weighted imaging contrast (KWIC) image reconstruction and it can be used with parallel imaging techniques. Quantitative tracer kinetic models can be formed allowing cerebral blood volume, cerebral blood flow and mean transit time to be estimated.
(Continued)

Vascular compliance can also be assessed using 4D dMRA by synchronizing dMRA acquisitions with the systolic and diastolic phases of the cardiac cycle.

11 Claims, 4 Drawing Sheets

Related U.S. Application Data

(60) Provisional application No. 61/731,278, filed on Nov. 29, 2012.

(51) Int. Cl.
   *G01R 33/563* (2006.01)
   *A61B 5/055* (2006.01)
   *G01R 33/56* (2006.01)
   *G01R 33/561* (2006.01)

(52) U.S. Cl.
   CPC ..... *G01R 33/4818* (2013.01); *G01R 33/4828* (2013.01); *G01R 33/5635* (2013.01); *G01R 33/56333* (2013.01); *G01R 33/4824* (2013.01); *G01R 33/5601* (2013.01); *G01R 33/5611* (2013.01); *G01R 33/5614* (2013.01)

(56) References Cited

U.S. PATENT DOCUMENTS

| | | | |
|---|---|---|---|
| 2002/0188206 A1* | 12/2002 | Davis | A61B 5/02007 600/485 |
| 2007/0112264 A1* | 5/2007 | Wu | A61B 5/0263 600/410 |
| 2009/0105582 A1 | 4/2009 | Dougherty et al. | |
| 2010/0304374 A1* | 12/2010 | Meijer | G01N 33/574 435/6.14 |
| 2011/0210732 A1 | 9/2011 | Worters et al. | |
| 2011/0260725 A1 | 10/2011 | Mordini et al. | |
| 2013/0113482 A1* | 5/2013 | Speier | G01R 33/4818 324/309 |

OTHER PUBLICATIONS

Yan et al., Unenhanced Dynamic MR Angiography: High Spatial and Temporal Resolution by Using True FISP-based Spin Tagging with Alternating Radiofrequency. Radiology. Jul. 2010; 256(1): 270-279.*

Spartano et al. "The relationship between carotid blood pressure relativity to mental stress and carotid inima-media thickness." Atherosclerosis. Oct. 2014 ; 236(2): 227-229.*

Komine et al.: Non-invasive assessment of arterial stiffness using oscillometric blood pressure measurement. BioMedical Engineering OnLine 2012 11:6.*

Chawla N.V. (2009) Data Mining for Imbalanced Datasets: An Overview. In: Maimon O., Rokach L. (eds) Data Mining and Knowledge Discovery Handbook. Springer, Boston, MA (Year: 2009).*

Yan et al. "Quantification of Arterial Cerebral Blood Volume Using Multiphase-Balanced SSFP-Based ASL." Magnetic Resonance in Medicine 68:130-139 (2012). First published online Nov. 29, 2011. https://doi.org/10.1002/mrm.23218 (Year: 2011).*

Winkelmann et al. "An Optimal Radial Profile Order Based on the Golden Ratio for Time-Resolved MRI." IEEE Transactions on Medical Imaging, vol. 26, No. 1: 68-76, Jan. 2007 (Year: 2007).*

Song et al. "Non-Contrast Enhanced 4-D Dynamic MRA with Golden Angle Radial Acquisition and K-space Weighted Image Contrast (KWIC) Reconstruction." Magn Reson Med. Dec. 2014 ; 72(6): 1541-1551. (Year: 2014).*

Pfefferbaum et al. "Volumetric Cerebral Perfusion Imaging in Healthy Adults—Regional Distribution, Laterality, and Repeatability of Pulsed Continuous Arterial Spin Labeling (PCASL)." Psychiatry Res. Jun. 30, 2010; 182(3): 266-273. (Year: 2010).*

Korean Intellectual Property Office (KIPO), International Search Report and Written Opinion, PCT International Appln. No. PCT/US2013/071590, dated Mar. 17, 2014, pp. 1-12, with claims searched, pp. 13-16, corresponding to U.S. Appl. No. 14/721,546 herein.

* cited by examiner

NONINVASIVE 4-D TIME-RESOLVED DYNAMIC MAGNETIC RESONANCE ANGIOGRAPHY

CROSS-REFERENCE TO RELATED APPLICATIONS

This application is a 35 U.S.C. § 111(a) continuation of PCT international application number PCT/US2013/071590 filed on Nov. 25, 2013, incorporated herein by reference in its entirety, which claims priority to, and the benefit of, U.S. provisional patent application Ser. No. 61/731,278 filed on Nov. 29, 2012, incorporated herein by reference in its entirety. Priority is claimed to each of the foregoing applications.

The above-referenced PCT international application was published as PCT International Publication No. WO 2014/085288 on Jun. 5, 2014, which publication is incorporated herein by reference in its entirety.

STATEMENT REGARDING FEDERALLY SPONSORED RESEARCH OR DEVELOPMENT

This invention was made with Government support under MH080892, awarded by the National Institutes of Health. The Government has certain rights in this invention.

INCORPORATION-BY-REFERENCE OF MATERIAL SUBMITTED IN A COMPUTER PROGRAM APPENDIX

Not Applicable

BACKGROUND OF THE INVENTION

1. Field of the Invention

This invention pertains generally to magnetic resonance imaging, and more particularly to a time-resolved, non-contrast enhanced, dynamic MRA (4D dMRA) technique that uses dynamic golden angle radial acquisitions and k-space weighted imaging contrast (KWIC) for image reconstruction that can be used in conjunction with parallel imaging techniques.

2. Description of Related Art

The evaluation of the dynamic flow patterns within the vasculature of the body is desirable for a number of clinical indications, such as steno-occlusive disease, arteriovenous malformation (AVM), and aneurysm. At the present time, intra-arterial digital subtraction angiography (DSA) is considered to be the reference standard for detecting and diagnosing these conditions that provides both high temporal and spatial resolution images of cerebral blood circulation and other vasculature. The DSA procedure, however, is invasive and requires the use of ionizing radiation (X-rays) as well as the injection of iodinated contrast media for imaging that has the associated risks of allergic and other adverse reactions.

Recently, contrast-enhanced dynamic MR angiography (CE-dMRA) has received considerable attention due to its ability to provide temporal information in addition to the otherwise "static" high-resolution 3-D contrast-enhanced MRA for a variety of clinical indications. However, the temporal resolution in CE-dMRA is generally on the order of seconds and the method also requires the intravenous injection of a contrast agent. In the standard MRA examination, 10 to 30 ml of a gadolinium-based contrast agent is typically injected at a flow rate of 1 to 3 mls/s. A test bolus technique is used to define the transit time. A data set is usually collected within 10 to 30 seconds of injection during the peak period of arterial enhancement by the presence of contrast.

In addition, it remains challenging to derive quantitative hemodynamic information using either the DSA and/or the CE-dMRA procedures. For example, imaging of some conditions such as arteriovenous malformations (AVM) requires frame rates greater than 1 frame per second and a special resolution greater than 1 mm in order to properly visualize the complex flow patterns and the vascular anatomy. Therefore, the X-ray DSA diagnostic procedure continues to be the clinical standard for diagnosing some conditions in spite of the undesirable use of ionizing radiation and potentially toxic contrast agents.

Non-contrast enhanced methods of magnetic resonance angiography have also been developed in an attempt to avoid the difficulties associated with acquisition timing, scanner limitations, inconsistent technician skill and contrast use with patients that have poor kidney function. However, past attempts to formulate schemes that reduce the time of acquisition and the amount of contrast exposure while increasing spatial resolution are usually at the expense of SNR and image quality.

Accordingly, there is a need for improved detection and diagnosis of cerebrovascular diseases with a magnetic resonance angiography method that has high spatial resolution for depicting the vascular architecture, as well as high temporal resolution for visualizing the dynamic blood flow patterns, while limiting or eliminating exposure to contrast agents or ionizing radiation.

The present invention satisfies this need as well as others and is generally an improvement over the art.

BRIEF SUMMARY OF THE INVENTION

The present invention provides a method with MR pulse sequences and post-processing algorithms for visualizing dynamic blood flow and quantifying hemodynamic parameters such as blood flow, blood volume and mean transit time that does not require the use of X-rays or contrast agents. The noninvasive 4D time-resolved dynamic MRA methods of the present invention are generally based on a combination of arterial spin labeling (ASL) with a cine multiphase balanced steady-state free precession (bSSFP) readout sequences.

In this framework, arterial spin labeling is used to magnetically label or tag arterial blood water as an endogenous tracer, and then the labeled bolus is continuously sampled at both high spatial (~1 mm$^3$) and temporal (50-100 ms) resolution. The general 4D dMRA pulse sequence consists of an ASL block followed by a multiphase SSFP readout. Variants of the multi-phase SSFP sequence can include the use of variable flip angles and Cartesian or non-Cartesian sampling strategies. Spin labeling can be implemented using pulsed, continuous and pseudo-continuous ASL schemes as well as velocity selective ASL.

However, compared to the standard arterial spin labeling (ASL) methods that offer a single physiological parameter (blood flow) at a single post-labeling delay time, the invention provides 4D dynamic information of blood flow with high temporal resolution and spatial resolution, as well as quantification of multiple hemodynamic parameters such as blood flow, blood volume and mean transit time. The use of accelerated imaging methods and enhanced/prolonged labeling bolus produces superior results compared to existing imaging methods due to higher imaging speed, spatio-temporal resolution and signal-to-noise ratio. The high temporal resolution (50-100 ms) of the technique allows the scan to be repeated as often as required during the same session.

The multi-phase bSSFP readout can be implemented (a) immediately or (b) after a selected time period of delay following the ASL pulse sequence. The series of SSFP images are preferably formed in a manner similar to cine MR imaging (i.e., an image for an individual time frame is generated from multiple segmented acquisitions synchronized to the labeling pulse).

By adjusting the delay time between labeling and readout pulse sequences, the inventive methods can focus on different vasculatures such as arteries, capillaries and veins. Label and control images of structures of interest can be acquired and compared such that the only difference between them is whether the inflowing arterial blood has been tagged.

The image post-processing preferably involves a pair-wise subtraction of label and control images at each time frame or phase. The series of subtracted images can be visualized as movies along axial, sagittal, coronal views or along any arbitrary angle. This technique has the flexibility to provide high resolution dynamic MR angiography (dMRA) similar to digital subtraction angiography (DSA), as well as lower resolution microvascular imaging similar to perfusion MRI.

In one embodiment, a dynamic radial acquisition with a golden angle view increment is used with the 4D dMRA method because of its high degree of efficiency and flexibility for retrospective dynamic image reconstruction. In another embodiment, a 3D stack-of-stars golden-angle radial acquisition in conjunction with temporal filtering strategies (k-space weighted image contrast or KWIC) is used to achieve ultrafast 4D dMRA with high spatial and temporal resolution, adequate SNR, and high temporal fidelity.

According to one aspect of the invention, a method for magnetic resonance angiography is provided that has high spatial resolution for depicting vascular architecture, as well as high temporal resolution for visualizing dynamic blood flow patterns.

Another aspect of the invention is to provide magnetic resonance imaging methods that are not invasive and do not require the use of ionizing radiation (X-ray) or the injection of iodinated contrast media.

A further aspect of the invention is to provide a system that can be adapted to several different diagnostic imaging applications such as for 1) visualizing and quantifying hemodynamics in cerebrovascular diseases such as arterio-venous malformation (AVM), steno-occlusive diseases and cerebral aneurysms; 2) integration of 4-D dynamic blood flow information in surgical planning; and 3) visualizing and quantifying hemodynamic changes during brain activation for functional MRI or in response to a pharmacological agent for pharmacological MRI.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes several embodiments of the magnetic resonance imaging methods of the present invention are described and depicted generally in FIG. 1 through FIG. 4. It will be appreciated that the methods may vary as to the specific steps and sequence and the apparatus architecture may vary as to structural details, without departing from the basic concepts as disclosed herein. The method steps are merely exemplary of the order that these steps may occur. The steps may occur in any order that is desired, such that it still performs the goals of the claimed invention.

Figure 1:
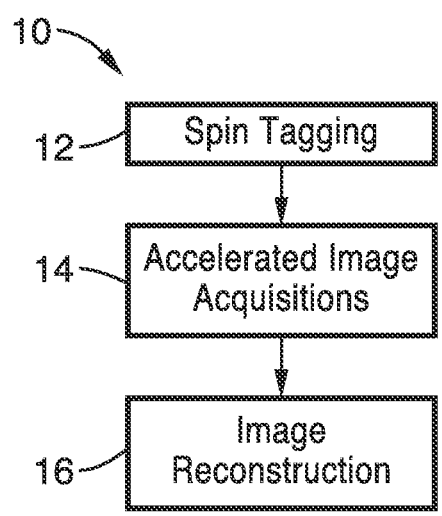
FIG. 1 is a flow diagram of a method for non-invasive 4D time resolved dynamic magnetic resonance angiography according to the invention.

Turning now to FIG. 1, a flow diagram of a method 10 for non-invasive 4D time resolved dynamic magnetic resonance angiography is schematically shown. The methods can be used with conventional magnetic resonance imagers with substantially homogeneous magnetic fields in the imaging space that are normally configured to evaluate living test subjects. The embodiment shown in FIG. 1 is directed to vascular imaging as an illustration of the methods.

At block 12 of FIG. 1, the arterial blood water is magnetically tagged or labeled as an endogenous tracer with an arterial spin labeling procedure. Spin labeling can be implemented using pulsed, continuous and pseudo-continuous ASL versions. However, velocity selective ASL is particularly preferred. Pulsed ASL for spin tagging is less preferred because the signal to noise ratio (SNR) is relatively low given its short duration. Pseudo-Continuous ASL can also be implemented to improve the SNR of 4D dMRA, however, at the cost of prolonged scan time, and a few initial phases of arterial inflow may be sacrificed.

To improve the image quality as well as to increase the temporal window for visualizing the full passage of dynamic blood flow over typical ASL, a multi-bolus dMRA technique is used that takes advantage of the phenomenon that the magnetization of balanced SSFP can be temporally stored along the z-axis by applying an $\pi/2$ pulse, while the magnetization preparation (spin tagging) is performed. The steady-state precession can then be resumed by applying another $\pi/2$ pulse as seen in the pulse sequence of FIG. 3. By applying a train of intermittent inversion pulses, multi-bolus dMRA offers a prolonged tagging bolus with increased SNR compared to the existing single-bolus dMRA. Pseudo-CASL based dMRA was performed for comparison which missed a few arterial inflow phases of dMRA.

With a prolonged/enhanced tagging bolus, multi-bolus pulsed ASL based dMRA can improve the visualization of draining veins of AVMs, for example. Multi-bolus ASL approaches can also be applied for perfusion imaging. However, shortcomings include uncertainties in the arterial input function and arterial transit time of the labeled blood due to variations in flow velocities across subjects. The multi-bolus dMRA technique of the invention may be applied in conjunction with multi-bolus ASL perfusion methods since the arterial input function can be obtained using multi-bolus dMRA in vivo. It is feasible to combine multi-bolus dMRA and perfusion imaging to improve the SNR and accuracy of quantitative perfusion MRI using ASL.

Figure 2A:
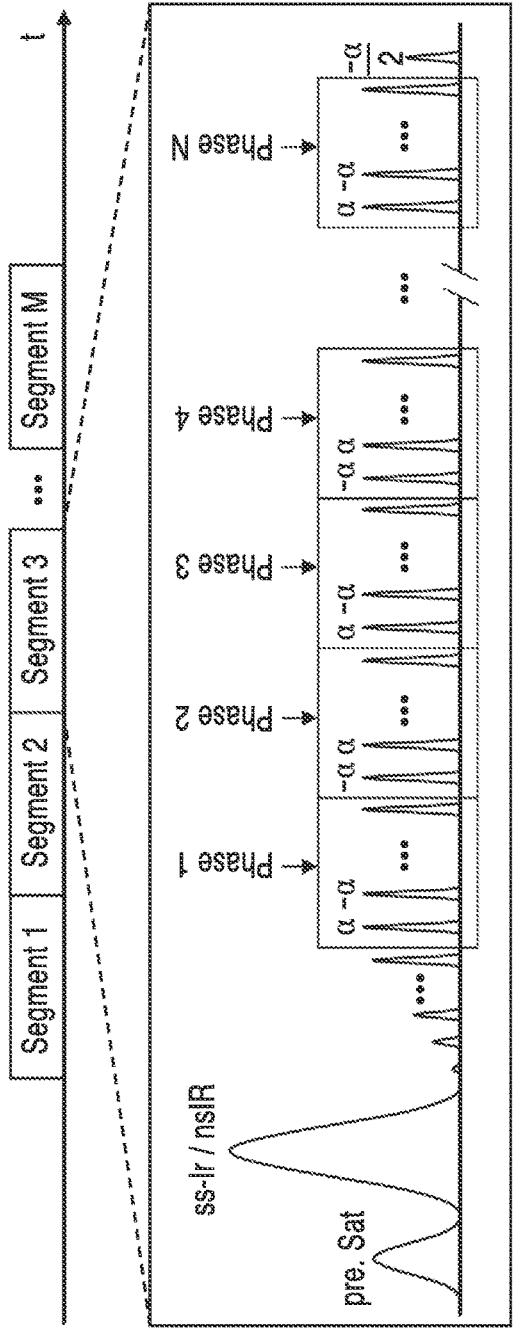
FIG. 2A is a pulse diagram of a variant of the 4D dMRA technique without a period of delay.

As illustrated in FIG. 2A, the general 4D dMRA pulse sequence 18 has an ASL block followed by a multiphase SSFP readout sequence. Suitable balanced steady-state free precession pulse sequences include TrueFISP, Balanced-FFE, FIESTA, and True SSFP sequences. The multiphase bSSFP readout sequence can be applied immediately after the ASL block as shown in sequence 18 of FIG. 2A or the readout sequence can be applied after a period of delay time as shown in sequence 20 of FIG. 2B. The delay time between the ASL and the readout pulse sequences can be adjusted to allow temporal enhancement of different vascular structures such as arteries, veins and capillaries.

Once the tagging is accomplished at block 12, the labeled bolus is sampled at block 14 of FIG. 1. The image acquisition times at block 14 are preferably accelerated to maximize the available spin label by the use of fast acquisition techniques. Accelerated imaging methods for 4D dMRA can include Cartesian sampling and non-Cartesian sampling approaches such as radial and spiral.

Both Cartesian and non-Cartesian sampling can be combined with parallel imaging which uses the spatial information inherent in the geometry of surface coil arrays to reduce scan time. Parallel imaging is an approach for reducing scan time that accounts for the local sensitivity of each coil in a phased array of the scanner. Each coil in the phased array receives data at the same time (i.e., in parallel). Parallel imaging includes techniques such as sensitivity encoding (SENSE) and generalized autocalibrating partially parallel acquisition (GRAPPA). Other parallel imaging techniques include the array spatial and sensitivity encoding technique (ASSET), the autocalibrating reconstruction for Cartesian sampling (ARC) technique, the integrated parallel acquisition technique (iPAT), and rapid acquisition through parallel imaging design (RAPID).

The preferred strategy for accelerated 4-D imaging involves using variable sampling rates for different spatial frequencies of k-space data without significant loss of fidelity of temporal information. View sharing is one approach in which the low frequency k-space data is updated more often than the high frequency k-space data, which is interpolated between consecutive time frames, thus leading to an effective shortening of the scan time. Subsequently, view sharing can be combined with elliptical centric encoding, keyhole, partial Fourier and/or parallel imaging to further improve the efficiency and spatiotemporal resolution.

In the preferred embodiment, dynamic golden angle radial acquisitions for 4D dMRA and k-space weighted imaging contrast (KWIC) are used for image reconstruction at block 16 of FIG. 1. As shown in the pulse sequence diagram of FIG. 4, subsequent radial profiles are separated by the golden angle (111.246°) which is optimal for flexible image reconstruction from an arbitrary number of profiles in radial MRI. For 4D dMRA, this acquisition allows advanced sliding window reconstructions with a flexible window size that can be adjusted according to the required spatial/temporal resolution.

Using KWIC imaging at block 16, the central k-space (which determines the image contrast) is sampled by the radial views of the time frame of interest ($T_{i-1}$, $T_i$), whereas the peripheral k-space is filled by radial views of neighboring time frames (similar to view sharing). KWIC can also be combined with parallel imaging methods.

One of the most appealing features of radial dMRA with KWIC is the high flexibility that allows many of the decisions regarding spatial/temporal resolution to be made retrospectively and optimally. For instance, a neurosurgeon can first view a static MRA with high spatial resolution based on all radial acquisitions, and then view temporal frames of dMRA at the temporal resolution of his or her choice.

The approach was initially verified with a single shot radial dMRA with an acceleration factor of 10 in imaging time (1 min) compared to standard Cartesian sampling that takes 10 minutes. Time courses in middle cerebral artery (MCA) regions of interest (ROIs) showed no observable temporal blurring in the radial dMRA images. There can be ghosting artifacts in Cartesian data likely due to cardiac pulsation effects which are invisible in radial dMRA images. High quality dMRA images were observed with a high temporal resolution and without apparent temporal blurring that were obtained in a fraction of the scan time of standard Cartesian based dMRA.

The enhanced/prolonged labeling bolus and accelerated imaging scheme for 4D dMRA permits modeling of quantitative tracer kinetics. One key advantage of the 4D dMRA technique is that the longitudinal magnetization of flowing blood is well preserved during multiphase SSFP scans. It has been observed that the multiphase SSFP ASL signals in arteries are identical to single-phase ASL signals and have no noticeable saturation effects. Observable saturation effects only occur in capillaries and tissue when blood flow slows down considerably and the T2/T1 ratio reduces, a phenomenon verified by Bloch equation simulation.

Therefore, the standard tracer kinetic model can be applied for estimating cerebral blood volume (CBV), cerebral blood flow (CBF) and mean transit time (MTT):

$$CBV = \frac{\int C(t)dt}{\int C_a(t)dt}$$

$$C(t) = CBF \cdot C_a(t) \otimes R(t)$$

$$MTT = CBV / CBF$$

where $C_a(t)$ and $C(t)$ are the concentration of labeled spins in the artery and each pixel respectively and $R(t)$ is the residual function.

More specifically, $C(t) = M(t) W(t) e^{t/T1\ blood}$, $C_a(t) = M(t) W(t) e^{t/T1\ blood}$ where $M_a(t)$ and $M(t)$ are measured signals in artery and each pixel respectively, $W(t)$ is a weighting factor to account for effects of flip angle. The $M_a(t)$ value can be measured from an artery or it can be assumed based on tagging duration and efficiency. CBF estimation relies on deconvolution using a singular value decomposition (SVD) or division in the frequency domain. Multi-parameter hemodynamic images of vascular subjects can be obtained quickly.

Accordingly, the obtained 4-D dynamic flow information and the calculated images of hemodynamic parameters can be integrated into the planning of stereotactic surgery, which currently does not include 4-D information. The method can also be applied for fMRI studies to visualize the dynamic blood flow responses and to quantify changes in hemodynamic parameters.

The invention may be better understood with reference to the accompanying examples, which are intended for purposes of illustration only and should not be construed as in any sense limiting the scope of the present invention as defined in the claims appended hereto.

Example 1

In order to demonstrate the functionality of the spin labeling aspects of the invention, a FISP-based spin tagging with alternating radiofrequencies (STAR) labeling sequence was evaluated and the spatial and temporal resolution of the method was optimized in eight healthy volunteers. In another six healthy volunteers, the contrast-to-noise ratio (CNR) and signal-to-noise ratio (SNR) of the STAR based dynamic MR angiography images were compared with those acquired by using a standard Look-Locker echo-planar technique by using the Wilcoxon signed rank test. Finally, one patient with an arteriovenous malformation (AVM) was studied using this technique.

Figure 2B:
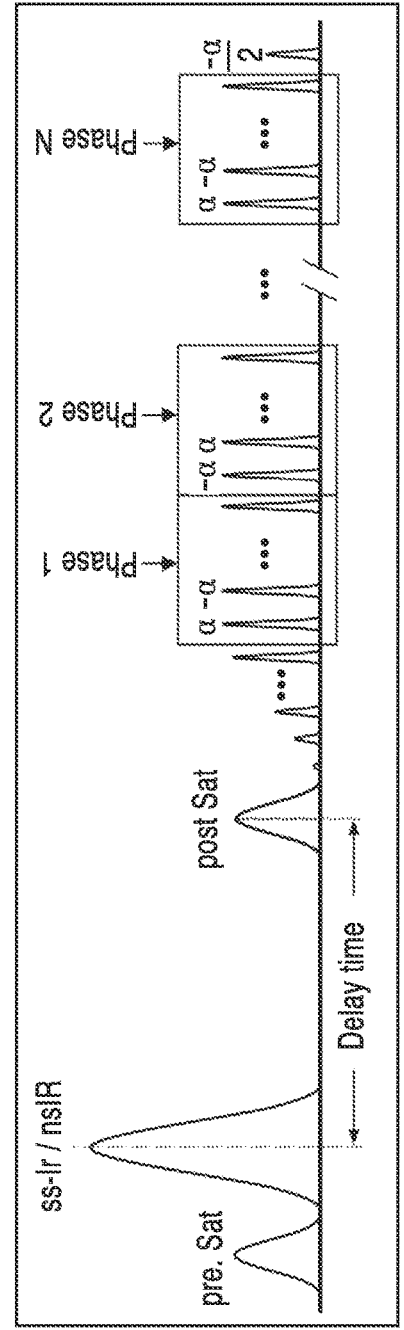
FIG. 2B is a pulse diagram with a period of delay before targeting specific vascular components (e.g. arteries, capillaries, or veins).
Figure 3:
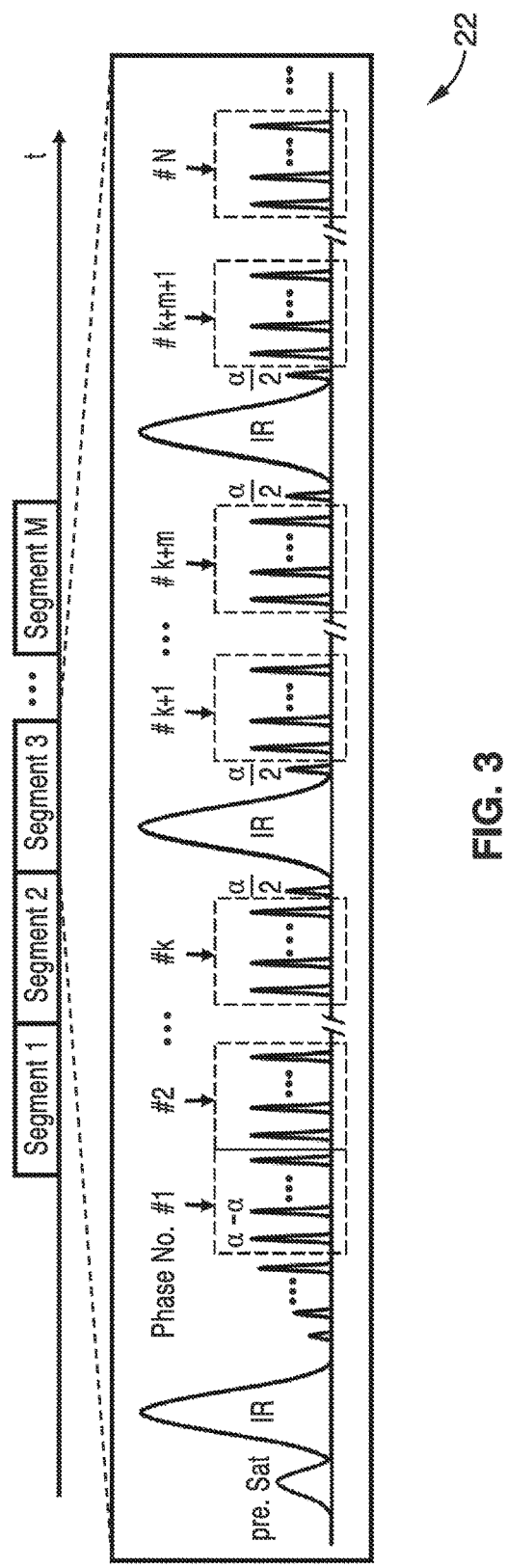
FIG. 3 is a pulse diagram for an illustrative pulse sequence for multi-bolus PASL dMRA.

As shown in the pulse sequence diagrams of FIG. 2A and FIG. 2B, immediately following a section-selective or non-selective hyperbolic secant inversion pulse, a train of 20 dummy radiofrequency pulses with Kaiser Bessel window ramp flip angles (i.e., $\alpha/21, -2\alpha/21, 3\alpha/21, \ldots, 20\alpha/21$) was applied to minimize transient signal oscillations. The signal was then continuously acquired by a segmented multiphase true FISP readout with the $\pm\alpha$ radiofrequency pulse scheme with phase encoding advancing in a centric order. At the end of the true FISP readout, the magnetization was restored to the positive z-axis by using an $\alpha/2$ pulse. The series of images were formed in a manner similar to cine MR imaging methods (i.e. an image for an individual time frame was generated from multiple segmented acquisitions synchronized to the labeling pulse). In this study, 11-21 k-space lines were acquired per segment, resulting in a temporal resolution of 50-100 msec for each time frame image.

Three consecutive experiments in healthy volunteers were conducted to optimize the STAR spin labeling technique. In all three experiments, images were acquired that cover the circle of Willis and associated main branch anatomical structures.

The first experiment determined the optimal gap between the labeling and imaging slab by measuring the arrival time of the labeling bolus as a function of the thickness of the selective inversion band. The thickness of the selective inversion pulse was set to 5, 10, and 15 times the imaging section thickness (5 mm).

In the second experiment, 3D STAR acquisitions with imaging resolution along the z-axis were performed to further improve the SNR due to volume excitation. A generalized, autocalibrating, partially parallel acquisition with an acceleration factor of two was applied to reduce the total imaging time to approximately 7 minutes while preserving a temporal resolution of 83 msec with 30 phases.

To investigate the effects of cardiac pulsation on dynamic MR angiography images, pulse-gated (electrocardiographically gated) 3D cine STAR imaging was performed. Depending on the cardiac cycle, 10-15 phases of dynamic MR angiography images with a temporal resolution of 52 msec were acquired within approximately 6 minutes.

The third experiment compared the STAR labeling with a standard dynamic MR angiography method based on a Look-Locker echo-planar imaging sequence with closely matched parameters. Three flip angles (a=20°, 40°, and 60°) were tested to investigate potential saturation effects in both techniques.

The SNR and CNR of the STAR tagged dynamic MR angiography images were 29% and 39% higher, respectively, compared with those acquired by using the standard Look-Locker echo-planar imaging sequence (both P=0.028). In the AVM patient, STAR dynamic MR angiography delineated the dynamic course of labeled blood flowing through feeding arteries into the nidus and draining veins.

Example 2

To further demonstrate the invention, two experiments were conducted with eight healthy volunteers (24.6±3.6 yrs, 3 males) on a Siemens TIM Trio 3T scanner. In the first experiment, a three-bolus STAR sequence was implemented with the time interval of 210, 315, 420 and 525 ms between inversion pulses respectively. The tagging was applied to an 80 mm slab inferior to the image slab with a 20 mm gap. The rest parameters were: FOV=220×165 mm$^2$, resolution=1× 1×1.5 mm$^3$, rate-2 GRAPPA; a 3D slab of 40 slices with 1.5 mm thickness, 22 phases from 150 to 2370 ms with a step of 105 ms was acquired within a total scan time of 7 minutes.

The second experiment made a comparison of the optimized multi-bolus dMRA with standard single-bolus PASL and pCASL based dMRA. The phase interval of 4 (420 ms) between inversion pulses was chosen for multi-bolus dMRA, with the rest parameters identical to the protocol used in the first experiment. For comparison, a standard single-bolus STAR sequence and pCASL based dMRA with a labeling duration of 300, 600 and 900 ms were performed using closely matched imaging parameters. DMRA images were generated by complex subtraction between label and control acquisitions, and maximum intensity projection (MIP) images were generated for each phase along three directions (transverse, sagittal, coronal).

The experiments validated the imaging parameters and the previous simulation results. In the simulations, the temporal profile of a labeled blood bolus can be described as a box-car function convoluted with a dispersion kernel. By incorporating T1 relaxation (m(t)), the signal of a labeled bolus can be expressed as $M_a(t)=2M_{0b}m(t)W'(t)$, where W'(t) is the temporal profile of the labeled bolus with dispersion which can be described by the Gaussian dispersion model. In the case of more than one tagging bolus, the interaction between two consecutive boluses was considered if the leading edge of the subsequent bolus occurs before the trailing edge of the preceding bolus. Single and three-bolus dMRA with different time intervals were simulated with a mean flow velocity of 20 cm/s, according to the measured mean flow velocity of 21 cm/s in internal carotid arteries from all the subjects using phase contrast MRI.

The results demonstrated that a prolonged bolus of labeled blood can be achieved using multi-bolus STAR labeling. Based on both simulation and experimental results, the optimal bolus interval should be around 400 ms to achieve a prolonged and continuous bolus of labeled blood in multi-bolus dMRA with a mean flow velocity of 20 cm/s. Accordingly, by combining the benefits of pulsed and pCASL based dMRA, the multi-bolus STAR technique can prolong and enhance the tagging bolus without sacrificing imaging speed or temporal resolution.

Example 3

The ultrafast 4D dMRA methods were further demonstrated with an embodiment employing a 3D stack-of-stars golden-angle radial acquisition in conjunction with temporal filtering strategies of k-space weighted image contrast (KWIC) to achieve 4D dMRA with high spatial and temporal resolution, adequate SNR, and high temporal fidelity. Dynamic radial acquisition with a golden angle view increment is ideally suited for 4D dMRA, given its high degree of efficiency and flexibility for retrospective dynamic image reconstruction.

Figure 4:
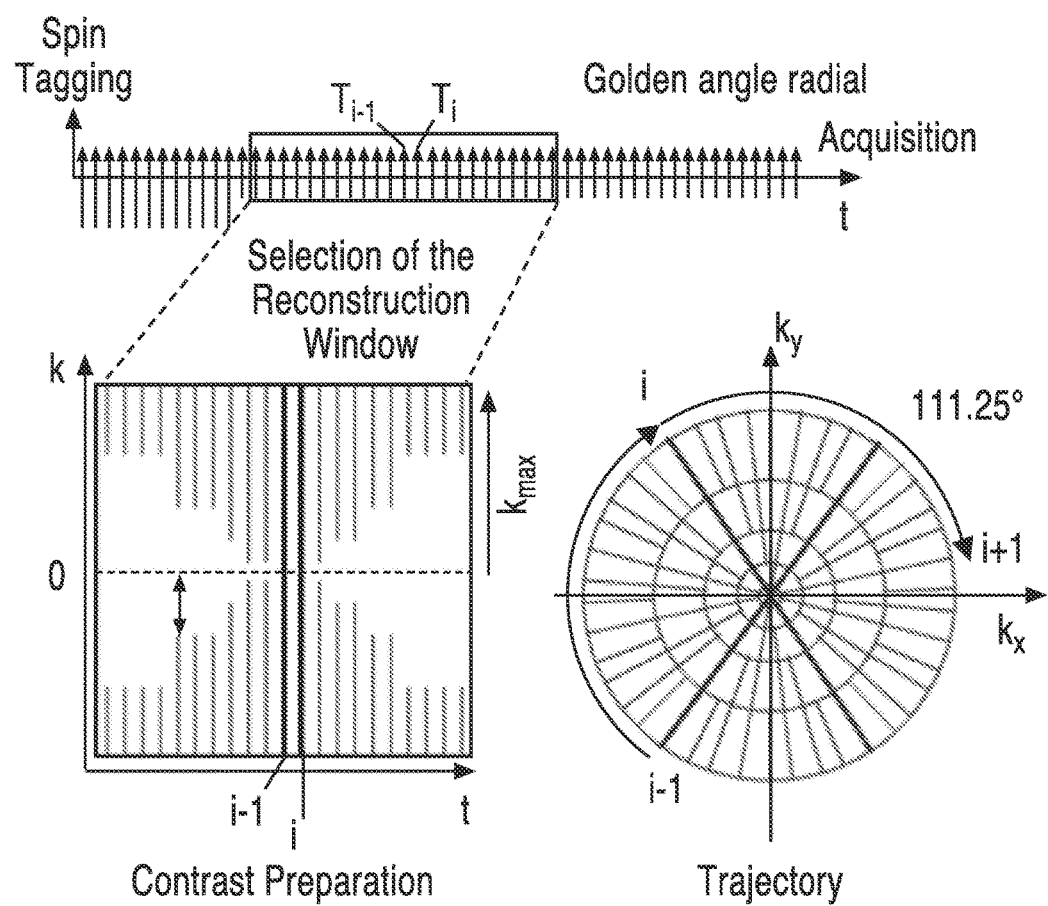
FIG. 4 is a diagram of 4D dMRA pulse sequence with dynamic golden angle acquisition and k-space weighted imaging contrast (KWIC) according to one embodiment of the invention.

The pulse sequence that was used consisted of a continuous 3D TrueFISP readout following either slice-selective or non-selective inversion pulses. A dynamic 3D radial stack-of-stars sampling with an in-plane view angle increment of $\theta_g=111.25°$ (golden angle) was utilized as illustrated in FIG. 4. A 3D radial stack-of-stars sampling was achieved by taking multiple shots, where each shot represented a slice-encoding step. The imaging parameters were as follows: FOV=256 mm, 500 views/shot, TR=4.58 ms, TE=TR/2, FA=30°, matrix=256×256, 32 mm×1.5 mm slices covering a significant portion of the brain, including the Circle of Willis and main branches, scan time=3 minutes.

Each temporal frame was reconstructed using 160 total views, with an effective temporal resolution of 100 ms (20-view window) via the KWIC filter. The KWIC reconstruction exploits the oversampling of the k-space center by encoding drastically fewer views in the central region of k-space (20 in this study). This reduction precipitated a proportionately large increase in temporal resolution since image contrast is determined primarily by the signal at the k-space center. The number of encoded views was systematically increased during the image reconstruction for more distant regions of k-space. A 3D-Cartesian version of the sequence with closely matched imaging parameters was also assessed for comparison. Thirty phases with a temporal resolution of 80 ms covering a 3D slab of 32 mm×1.5 mm sections (rate-2 GRAPPA) were acquired within a total scan time of 10 minutes.

Many dMRA maximum intensity projection (MIP) images were acquired at 7 phases using 3D-radial and Cartesian acquisitions and evaluated. The dynamic blood flow pattern through the Circle of Willis and its main braches could be clearly visualized by radial dMRA, including small distal branches of the middle cerebral artery (MCA) and posterior cerebral artery (PCA). Compared to Cartesian dMRA, the background tissue signal was markedly suppressed in the radial dMRA process, resulting in sharp MRA images throughout the temporal phases. The contrast-to-noise ratio (CNR) between radial (CNR=9.6) and Cartesian (CNR=11.7) dMRA were comparable, although the scan time of radial dMRA was less than one third of that of the Cartesian dMRA. The mean dMRA time course in the MCA demonstrated excellent agreement between radial and Cartesian acquisitions.

Accordingly, the speed of golden angle radial acquisition and the flexibility of KWIC with 3D stack-of-stars TrueFISP acquisitions in 4D dMRA can dramatically reduce the scan time compared to conventional methods, while maintaining a high spatial and temporal resolution.

Example 4

The diagnostic methods of the invention can be adapted to many different imaging contexts. For example, the methods can be used to estimate vascular compliance or stiffness of the vessel. A reduction in vascular compliance (VC) is a risk factor and/or marker of a number of diseases with high social and economical impact, such as atherosclerosis, hypertension, and diabetes. Aging is also accompanied by a decrease of VC. Currently, VC can be indirectly estimated by measuring aortic pulse wave velocity (PWV) with ultrasound imaging and MRI. To date, however, no method is available for assessing intracranial VC, which is defined by the change in arterial blood volume ($\Delta BV$) due to a given change in arterial blood pressure ($\Delta BP$), i.e., VC=$\Delta BV/\Delta BP$.

It is possible to assess vascular compliance using 4D dMRA by synchronizing the dMRA acquisitions with the systolic and diastolic phases of the cardiac cycle. This was demonstrated by measuring the blood flow velocities in internal carotid arteries (ICA) using an ECG-triggered time-resolved phase contrast MRI. The time delays at peak systole and early diastole were identified in each individual subject. Two ECG-triggered dMRA scans were performed with pulsed ASL applied at the peak systolic and early diastolic phases, respectively. Arterial CBV at systolic and diastolic phases were calculated based on the tracer kinetic model described previously. The VC was calculated as $\Delta BV/\Delta BP$, where $\Delta BV$ was the difference in arterial CBV between systolic and diastolic phases, and $\Delta BP$ was the difference in brachial blood pressure between systolic and diastolic phases.

The mean time courses of multi-phase SSFP and Look-Locker-EPI ASL signals with spin tagging applied at the peak systolic and early diastolic phases in big arteries (>5%), small arteries/arterioles (1-5%), and capillary/tissue respectively were evaluated.

Look-Locker-EPI ASL was performed to estimate any changes in capillary/tissue perfusion between systolic and diastolic phases. Elevated labeled blood signals were observed for the peak systolic time courses in big arteries as well as in small arteries and arterioles, compared to those of the early diastolic phase. However, there was no significant difference between dynamic capillary/tissue perfusion signals at systolic and diastolic phases, respectively.

A map of CBV changes between systole and diastole from a representative subject was created. CBV increases could be observed mainly in arteries, and to a lesser extent in small arteries and arterioles. Under the assumption of an average whole brain volume of 1300 mL (can be accurately measured on structural MRI), absolute arterial CBV values were obtained in big arteries and small arteries/arterioles. Then the VC was calculated by $\Delta CBV$ divided by $\Delta BP$ (0.15 mL/mmHg in big arteries, and 0.07 mL/mmHg in small arteries and arterioles).

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A method of 4D time resolved dynamic magnetic resonance angiography comprising: (a) magnetically labeling a volume of blood water of a test subject; (b) acquiring a plurality of magnetic resonance imaging data sets of the labeled subject from a magnetic resonance scanner with a fast acquisition using balanced steady state free precession pulses and k-space under-sampling; and (c) reconstructing images from the acquired data sets to provide a set of magnetic resonance images.

2. A method as recited in any previous embodiment, wherein the magnetically labeling is implemented with an arterial spin labeling technique selected from the group of techniques consisting of pulsed arterial spin labeling, continuous arterial spin labeling, velocity selective arterial spin labeling and pseudo-continuous arterial spin labeling.

3. A method as recited in any previous embodiment, wherein the acquiring a plurality of magnetic resonance imaging data sets comprises performing an acquisition procedure selected from the group of acquisition procedures consisting of Cartesian sampling with parallel imaging, non-Cartesian sampling with parallel imaging, Cartesian sampling and non-Cartesian sampling.

4. A method as recited in any previous embodiment, wherein the acquisition procedure further comprises view sharing to further shorten required scan times.

5. A method as recited in any previous embodiment, wherein the acquiring a plurality of magnetic resonance imaging data sets comprises performing an acquisition procedure is a dynamic golden angle radial acquisition.

6. A method as recited in any previous embodiment, wherein the reconstructing images from the acquired data sets is a k-space weighted imaging contrast (KWIC) reconstruction.

7. A method as recited in any previous embodiment, further comprising: (a) forming quantitative tracer kinetic models from reconstructed images; and (b) estimating cerebral blood volume (CBV), cerebral blood flow (CBF) and mean transit time (MTT) with the models and image data sets.

8. A method as recited in any previous embodiment, further comprising: (a) synchronizing dynamic magnetic resonance angiography acquisitions with systolic and diastolic phases of the cardiac cycle; (b) forming quantitative tracer kinetic models from reconstructed images; (c) estimating cerebral blood volume (CBV) at systolic and diastolic phases with the tracer kinetic models; (d) calculating the difference in arterial blood volume ($\Delta V$) and brachial blood pressure ($\Delta BP$) between systolic and diastolic phases; and (e) assessing vascular compliance by calculating $\Delta BV/\Delta BP$.

9. A method of 4D time resolved dynamic magnetic resonance angiography, comprising: (a) magnetically labeling a volume of blood water of a test subject; (b) acquiring a plurality of magnetic resonance imaging data sets of the labeled subject from a magnetic resonance scanner with a golden-angle radial acquisition; and (c) reconstructing images from the acquired data sets with a k-space weighted image contrast (KWIC) reconstruction to provide a set of magnetic resonance images.

10. A method as recited in any previous embodiment, wherein the magnetically labeling is implemented with an arterial spin labeling technique selected from the group of techniques consisting of pulsed arterial spin labeling, continuous arterial spin labeling, velocity selective arterial spin labeling and pseudo-continuous arterial spin labeling.

11. A method as recited in any previous embodiment, wherein the magnetically labeling is implemented with TrueFISP based spin tagging with alternating radiofrequency pulses.

12. A method as recited in any previous embodiment, further comprising: (a) forming quantitative tracer kinetic models from reconstructed images; and (b) estimating cerebral blood volume (CBV), cerebral blood flow (CBF) and mean transit time (MTT) with the models and image data sets.

13. A method as recited in any previous embodiment, further comprising: (a) synchronizing dynamic magnetic resonance angiography acquisitions with systolic and diastolic phases of the cardiac cycle; (b) forming quantitative tracer kinetic models from reconstructed images; (c) estimating cerebral blood volume (CBV) at systolic and diastolic phases with the tracer kinetic models; (d) calculating the difference in arterial blood volume ($\Delta BV$) and brachial blood pressure ($\Delta BP$) between systolic and diastolic phases; and (e) assessing vascular compliance by calculating $\Delta BV/\Delta BP$.

14. A method of 4D time resolved dynamic magnetic resonance angiography, comprising: (a) placing a subject into a substantially homogeneous magnetic field in the imaging space of a magnetic resonance imager; (b) applying an arterial spin labeling pulse sequence; (c) applying a balanced steady-state free precession pulse sequence; and (d) reconstructing a series of magnetic resonance images from multiple acquisitions synchronized to the labeling pulse.

15. A method as recited in any previous embodiment, further comprising delaying the application of the balanced steady-state free precession pulse sequence for a period of time after the application of the arterial spin labeling pulse sequence.

16. A method as recited in any previous embodiment, wherein the arterial spin labeling pulse sequence is selected from the group of pulse sequences consisting of pulsed arterial spin labeling sequences, continuous arterial spin labeling pulse sequences, velocity selective arterial spin labeling pulse sequences and pseudo-continuous arterial spin labeling pulse sequences.

17. A method as recited in any previous embodiment, wherein the balanced steady-state free precession pulse sequence is selected from the group of pulse sequences consisting of TrueFISP, Balanced-FFE, FIESTA, and True SSFP.

18. A method as recited in any previous embodiment, wherein the balanced steady-state free precession pulse sequence further comprises variable flip angles.

19. A method as recited in any previous embodiment, further comprising incorporating parallel imaging.

20. A method as recited in any previous embodiment, wherein the parallel imaging comprises a technique selected from the group of parallel imaging techniques consisting of sensitivity encoding (SENSE), generalized autocalibrating partially parallel acquisition (GRAPPA), array spatial and sensitivity encoding technique (ASSET), autocalibrating reconstruction for Cartesian sampling (ARC), integrated parallel acquisition technique (iPAT), and rapid acquisition through parallel imaging design (RAPID).

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method of estimating arterial stiffness or vascular compliance of internal carotid arteries and branches using 4D time resolved dynamic magnetic resonance angiography, the method comprising:
   (a) magnetically labeling a volume of blood water of a test subject;
   (b) acquiring a plurality of magnetic resonance imaging data sets of vasculature of the test subject containing labeled blood water with a magnetic resonance scanner with a fast acquisition using balanced steady state free precession pulses and k-space under-sampling;
   (c) reconstructing images from the acquired data sets to provide a set of magnetic resonance images;
   (d) synchronizing dynamic magnetic resonance angiography acquisitions with systolic and diastolic phases of the cardiac cycle;
   (e) forming quantitative tracer kinetic models from reconstructed images;
   (f) estimating cerebral blood volume (CBV) at systolic and diastolic phases with the tracer kinetic models;
   (g) calculating the difference in arterial blood volume ($\Delta$BV) of internal carotid arteries and branches and brachial blood pressure ($\Delta$BP) difference between systolic and diastolic phases; and
   (h) assessing vascular compliance of the subject by calculating $\Delta$BV/$\Delta$BP.

2. A method as recited in claim 1, wherein said magnetically labeling is implemented with an arterial spin labeling technique selected from the group of techniques consisting of pulsed arterial spin labeling, continuous arterial spin labeling, velocity selective arterial spin labeling and pseudo-continuous arterial spin labeling.

3. A method as recited in claim 1, wherein said acquiring a plurality of magnetic resonance imaging data sets comprises performing an acquisition procedure selected from the group of acquisition procedures consisting of Cartesian sampling with parallel imaging, non-Cartesian sampling with parallel imaging, Cartesian sampling and non-Cartesian sampling.

4. A method as recited in claim 3, wherein said acquisition procedure further comprises view sharing to further shorten required scan times.

5. A method as recited in claim 1, wherein said acquiring a plurality of magnetic resonance imaging data sets comprises a dynamic golden angle radial acquisition.

6. A method as recited in claim 1, wherein said acquiring a plurality of magnetic resonance imaging data sets comprises a dynamic golden angle radial acquisition and reconstructing images from the acquired data sets comprises a k-space weighted imaging contrast (KWIC) reconstruction.

7. A method as recited in claim 1, further comprising:
   (a) forming quantitative tracer kinetic models from reconstructed images; and
   (b) estimating cerebral blood volume (CBV), cerebral blood flow (CBF) and mean transit time (MTT) with the models and image data sets.

8. A method of 4D time resolved dynamic magnetic resonance angiography to estimate arterial stiffness or vascular compliance of internal carotid arteries and branches, the method comprising:
   (a) magnetically labeling a volume of blood water of a test subject;
   (b) acquiring a plurality of magnetic resonance imaging data sets of the vasculature of the test subject containing labeled blood water with a magnetic resonance scanner with a golden-angle radial acquisition;
   (c) reconstructing images from the acquired data sets with a k-space weighted image contrast (KWIC) reconstruction to provide a set of magnetic resonance images
   (d) synchronizing dynamic magnetic resonance angiography acquisitions with systolic and diastolic phases of the cardiac cycle;
   (e) forming quantitative tracer kinetic models from reconstructed images;
   (f) estimating cerebral blood volume (CBV) at systolic and diastolic phases with the tracer kinetic models;
   (g) calculating the difference in arterial blood volume ($\Delta$BV) of internal carotid arteries and branches and brachial blood pressure ($\Delta$BP) difference between systolic and diastolic phases; and
   (h) assessing vascular compliance of the subject by calculating $\Delta$BV/$\Delta$BP.

9. A method as recited in claim 8, wherein said magnetically labeling is implemented with an arterial spin labeling technique selected from the group of techniques consisting of pulsed arterial spin labeling, continuous arterial spin labeling, velocity selective arterial spin labeling and pseudo-continuous arterial spin labeling.

10. A method as recited in claim 8, wherein said magnetically labeling is implemented with TrueFISP based spin tagging with alternating radiofrequency pulses.

11. A method as recited in claim 8, further comprising:
  (a) forming quantitative tracer kinetic models from reconstructed images; and
  (b) estimating cerebral blood volume (CBV), cerebral blood flow (CBF) and mean transit time (MTT) with the models and image data sets.

\* \* \* \* \*